United States Patent [19]

Hakky

[11] Patent Number: 4,657,018

[45] Date of Patent: Apr. 14, 1987

[54] AUTOMATIC/MANUAL RESECTOSCOPE

[76] Inventor: Said I. Hakky, 185 Dagenham Road, Rush Green, Romford, Essex RM7 OTL, England

[21] Appl. No.: 660,594

[22] Filed: Oct. 15, 1984

Related U.S. Application Data

[63] Continuation-in-part of Ser. No. 524,814, Aug. 19, 1983, abandoned.

[51] Int. Cl.[4] .............................................. A61B 17/39
[52] U.S. Cl. ............................ 128/303.15; 128/303.17
[58] Field of Search ........... 128/303.1, 303.12, 303.13, 128/303.14, 303.15, 303.17

[56]       References Cited
       U.S. PATENT DOCUMENTS

| | | | |
|---|---|---|---|
| 2,068,721 | 1/1937 | Wappler et al. | 128/303.17 |
| 2,442,966 | 6/1948 | Wallace | 128/303.17 |
| 2,487,502 | 11/1949 | Willinsky | 128/303.14 |
| 2,545,865 | 3/1951 | Wallace | 128/303.17 |
| 3,100,489 | 8/1963 | Bagley | 128/303.17 |
| 3,149,633 | 9/1964 | Zingale | 128/303.17 |
| 3,763,864 | 10/1973 | Dremann | 128/303.17 |
| 4,196,734 | 4/1980 | Harris | 128/303.17 |
| 4,311,145 | 1/1982 | Esty et al. | 128/303.17 |
| 4,418,692 | 12/1983 | Guay | 128/303.17 |

FOREIGN PATENT DOCUMENTS

| | | | |
|---|---|---|---|
| 452125 | 10/1948 | Canada. | |
| 2239336 | 2/1974 | Fed. Rep. of Germany | 128/303.17 |
| 1437414 | 5/1976 | United Kingdom | 128/303.17 |

Primary Examiner—Edward M. Coven
Assistant Examiner—David Shay
Attorney, Agent, or Firm—Caesar, Rivise, Bernstein, Cohen & Pokotilow, Ltd.

[57]        ABSTRACT

A resectoscope having a linearly movable cutting element mounted for reciprocating motion while an outer sheath adapted to be inserted into the urethra employs a power source for automatically reciprocating the cutting element when the source is energized, control means actuatable by the user for energizing the power source, heating means for transmitting electrical current to the cutting element and timing means for intemittently energizing the heating means so taht the heating means is energized during the cutting stroke of the cutter. In accordance with another aspect of the invention the resectoscope includes a hand actuatable lever for manually reciprocating the cutting element independently of the operation of the power source.

17 Claims, 21 Drawing Figures

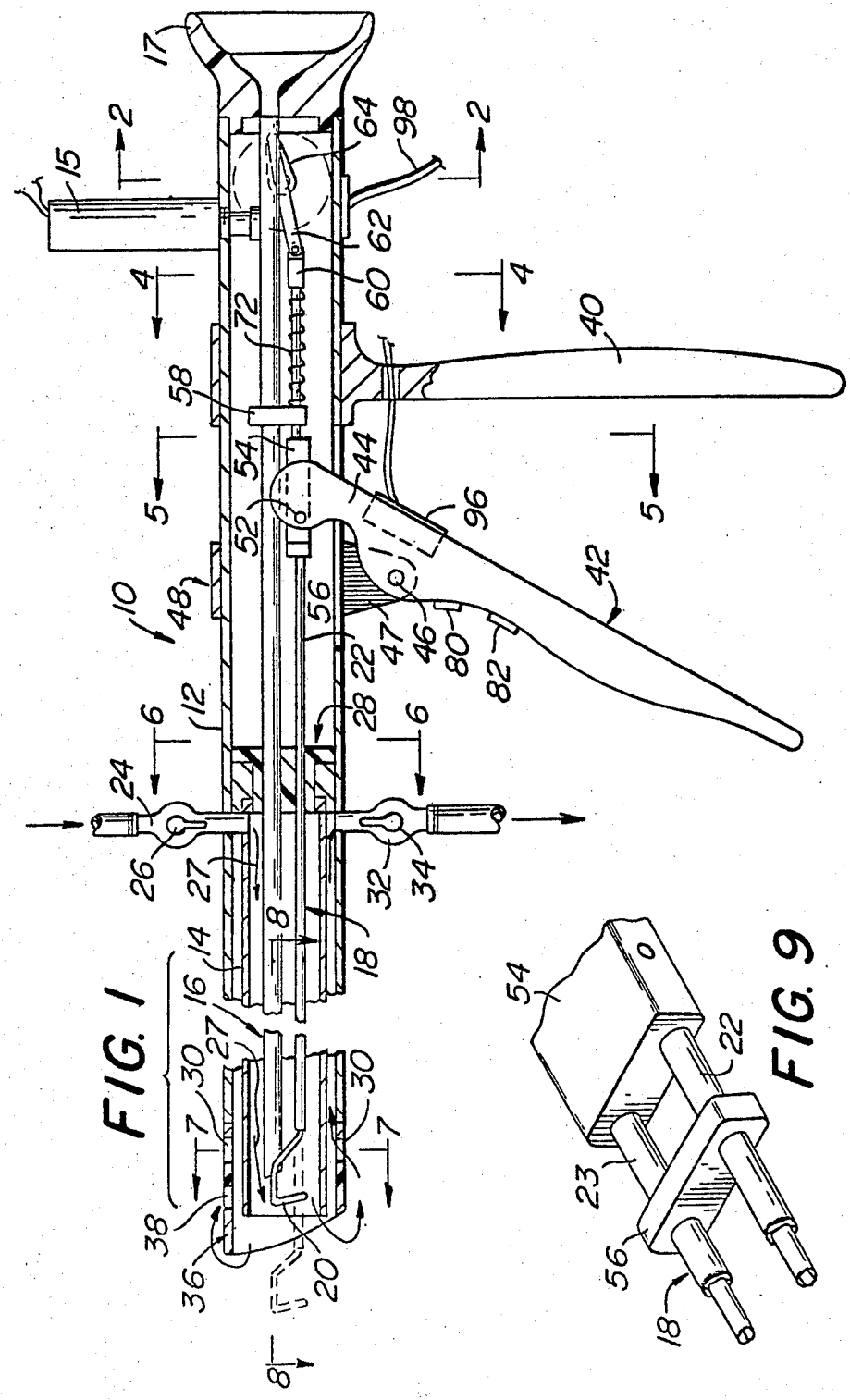

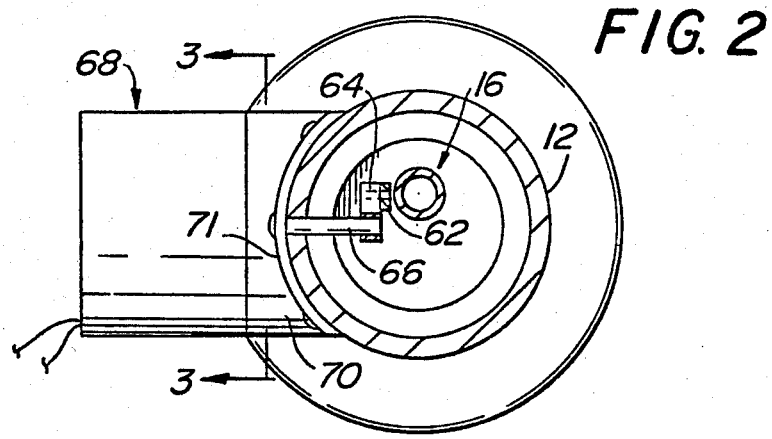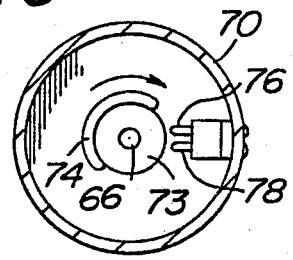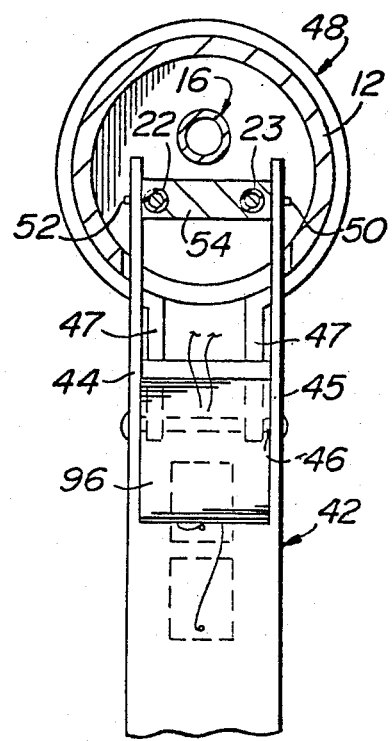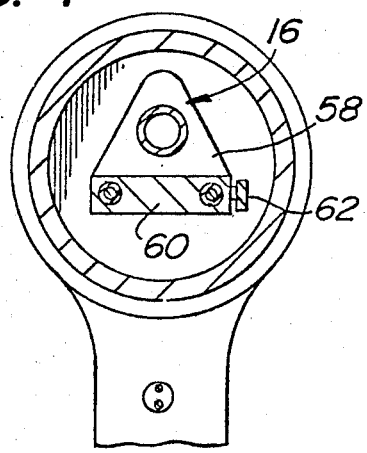

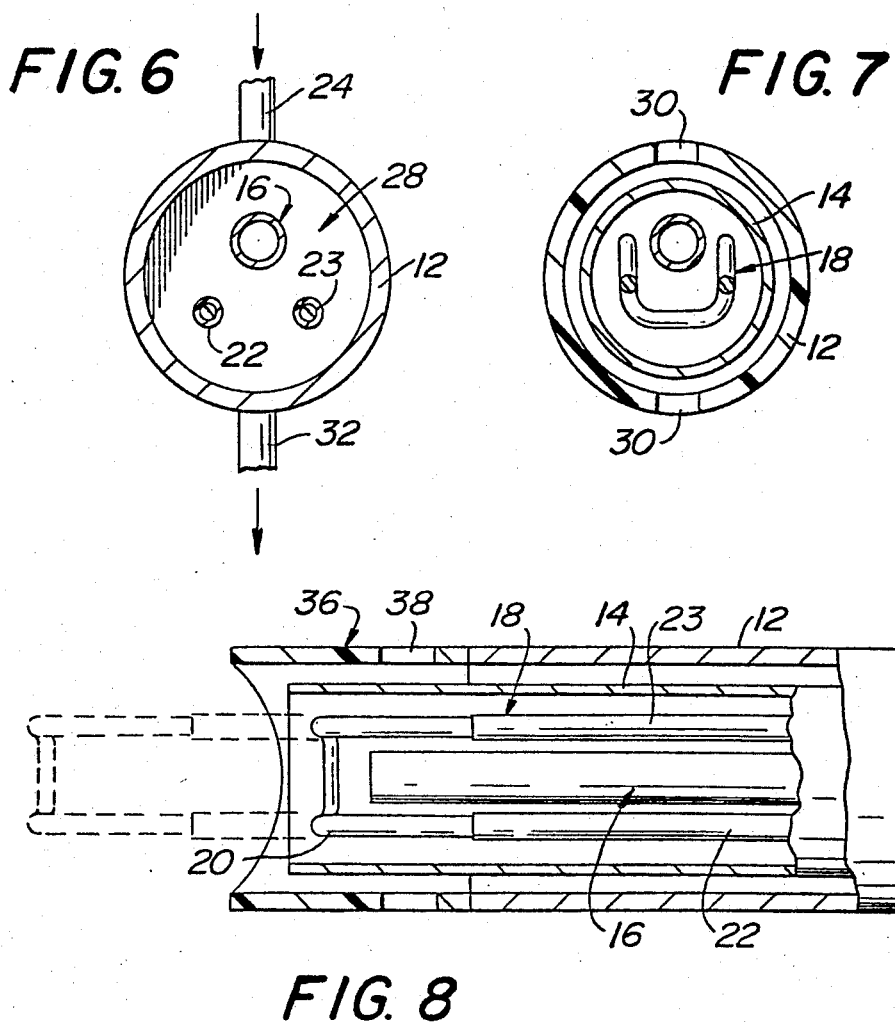

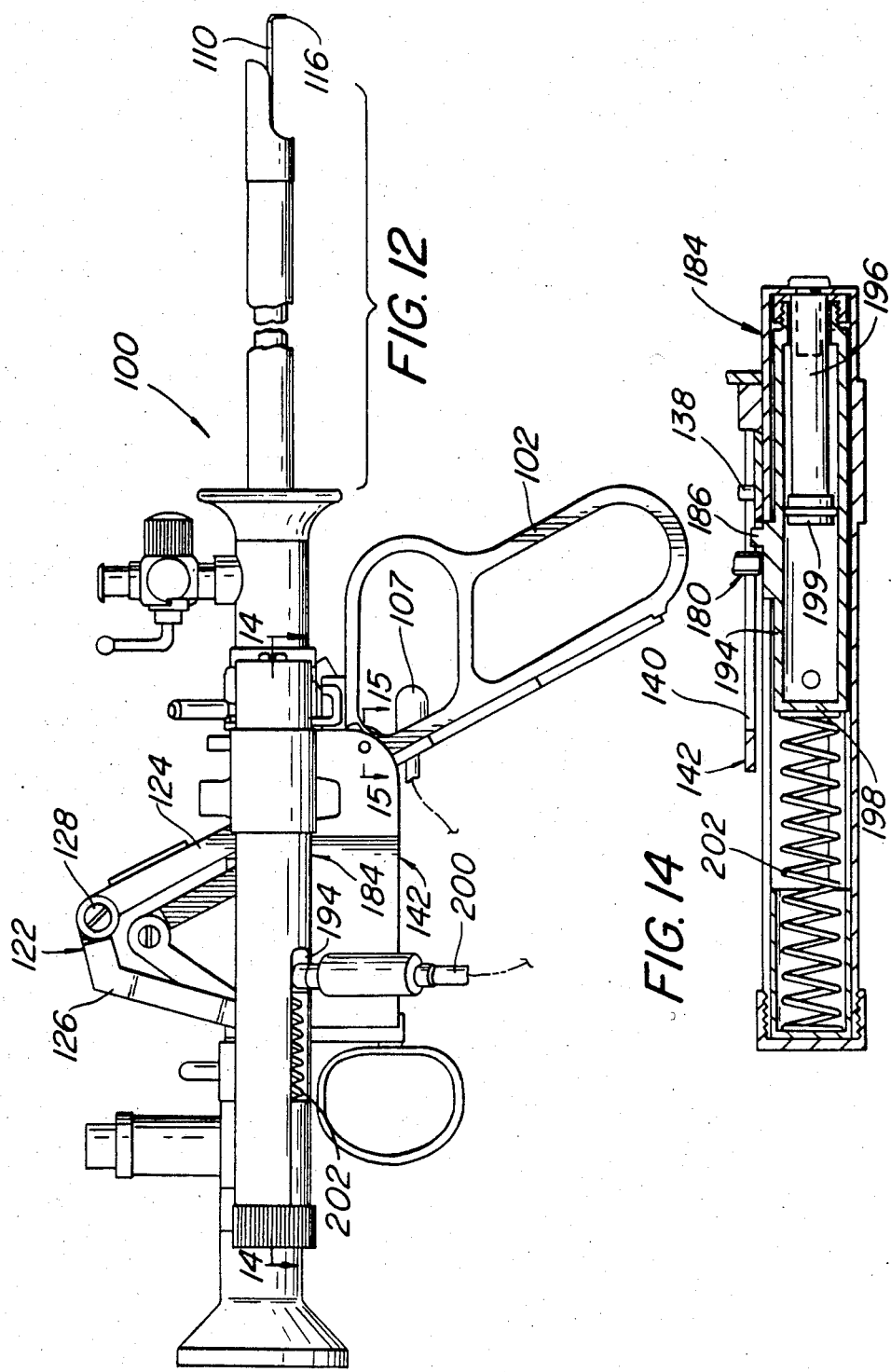

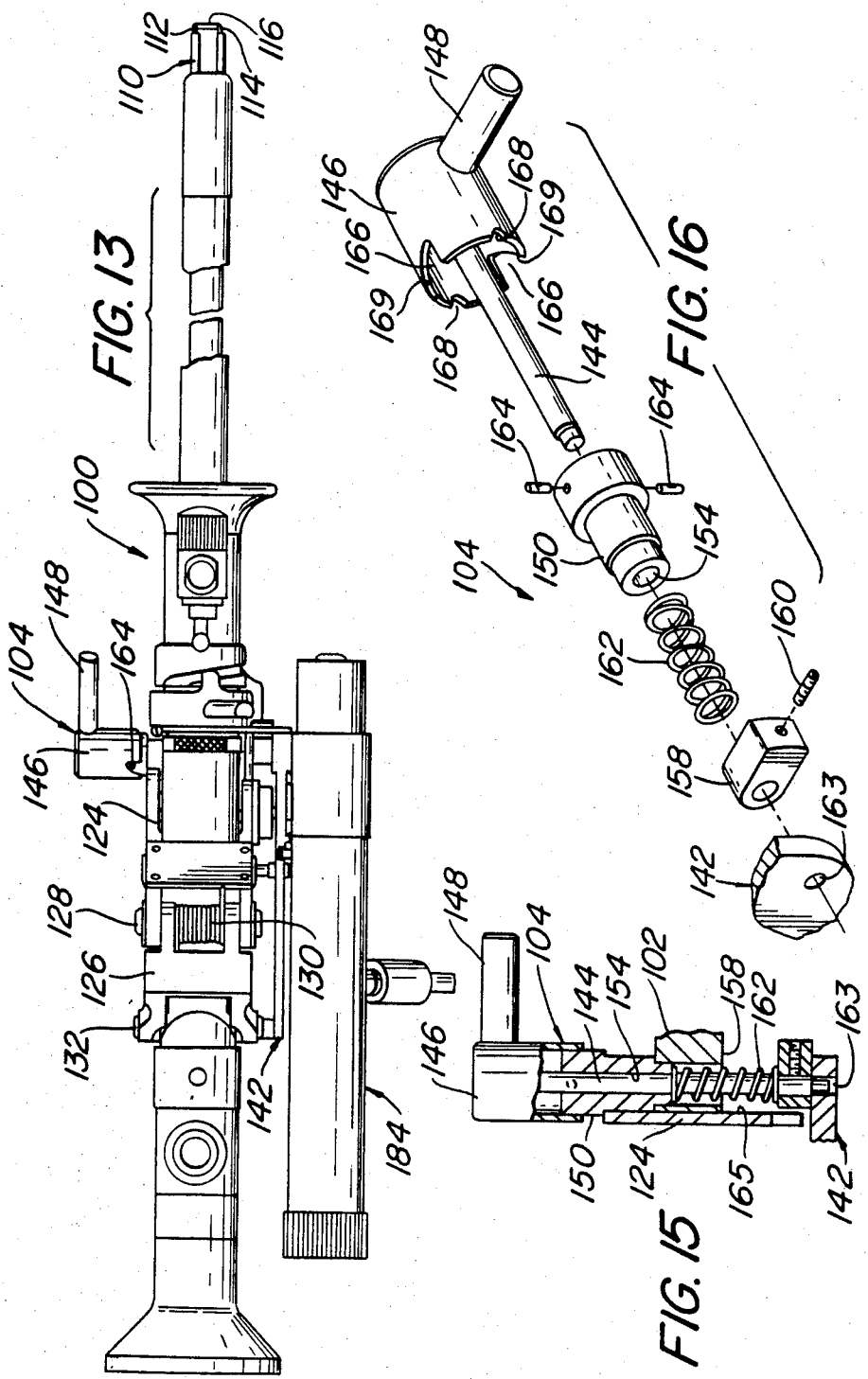

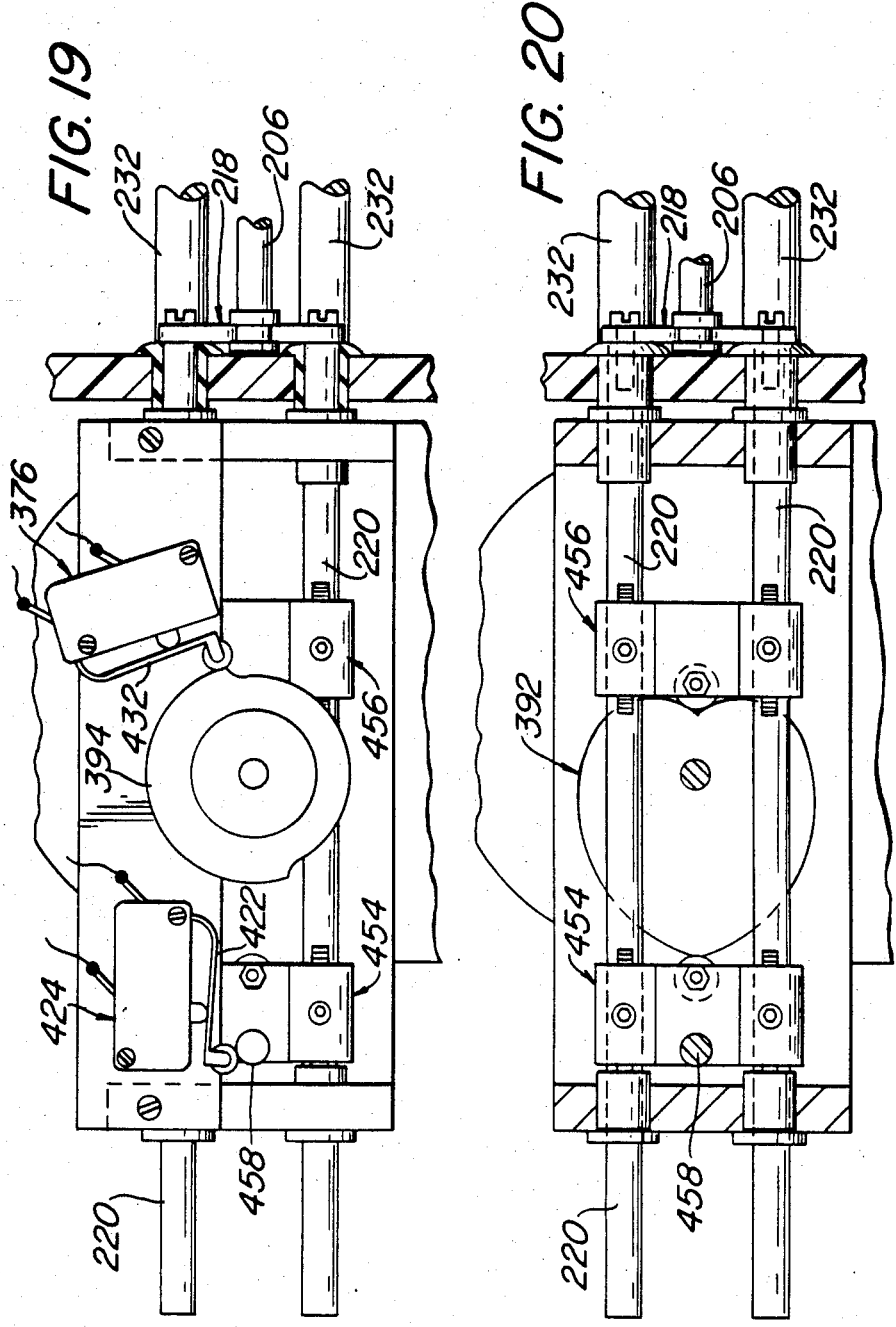

AUTOMATIC/MANUAL RESECTOSCOPE

RELATED APPLICATIONS

This application is a continuation-in-part of U.S. application Ser. No. 524,814, filed Aug. 19, 1983 now abandoned and entitled Automatic/Manual Resectoscope.

BACKGROUND OF THE INVENTION

This invention relates generally to the field of surgical devices, and more specifically to a resectoscope.

A resectoscope is employed transurethrally to perform prostate and/or bladder surgery. This device has an elongate section provided with an outer sheath, generally made of stainless steel, which is inserted into the urethra. The outer sheath prevents the urethra from contracting, while working elements internally of the sheath are employed to cut away the desired tissue.

Conventional resectoscopes either are of the cold punch type, wherein the cutting element is unheated, or are of the heated type, wherein a cutting element, in the form of a conductive wire, is heated through an electrical connection to a diathermy unit. The diathermy unit can be controlled by the surgeon, either through the use of a hand-operated switch, or through the use of a foot-operated switch.

In a manually operated resectoscope of the type employing a heated cutting element the surgeon manually extends the cutting element beyond the end of the outer sheath to a position engaging the tissue to be cut. Thereafter, the cutting element is energized through actuation of the diathermy unit, and at the same time the cutting element is manually retracted to cause it to slice away a desired chunk of the tissue. The surgeon views the area being operated upon through a telescopic system that also is mounted within the stainless steel sheath of the device, and a continuous irrigation system is utilized to keep the line-of-sight free of blood and other debris.

During prostate surgery it is common to cut away approximately 1/10 of a gram of tissue with each cutting stroke of the resectoscope. Although the total weight of tissue to be removed varies with the size of the individual and the severity of the problem, it is quite common to remove anywhere from 20 to 150 grams of tissue in a typical prostate operation. Therefore, in even the simplest of operations, it is generally necessary to reciprocate the cutting element at least 200 times.

In a convention manual resectoscope this will require the surgeon to manually extend the cutting element outwardly of the protective sheath, and then manually retract the element through its tissue-cutting stroke, while at the same time applying heat to the cutting element by the manual actuation of the diathermy unit. Obviously, carrying out these manual steps 600 or more times in a single operation is a time consuming and tiring procedure.

Although it may be desirable during various phases of the surgical procedure to manually control the reciprocation and heating of the cutting element of the resectoscope, other phases of the procedure, and in many cases the entire surgical procedure, could be carried out by an automatic system, wherein the cutting element is automatically reciprocated at a desired cutting frequency under control of a separate power source. To the best of applicant's knowledge there are no presently existing resectoscopes which are capable of both manual and automatic operation. In other words, the prior art resectoscopes are either designed to be manually operated or automatically operated. However, there is no single resectoscope which can be adapted for either automatic or manual operation.

Moreover, although there are teachings in the prior art of automatically operated resectoscopes, they either are of the cold-punch type, wherein the cutting element is not heated, or the cutting element is constantly heated during all portions of its reciprocating stroke. In other words, applicant is not aware of any prior art resectoscopes in which the cutting element is automatically reciprocated, but only selectively heated during the cutting part of the reciprocating stroke.

Canadian Pat. No. 452,125, issued to Wallace, discloses a resectoscope employing a motor (not shown) which is controlled by a switch to automatically reciprocate a cutting element. The switch also functions to complete the heating circuit, whereby the cutting tip will be constantly heated while it is being reciprocated. In other words, the Wallace device does not provide any arrangement for intermittently applying current to the cutting tip, let alone intermittently applying the current to the tip in a timed relationship with the cutting stroke. Moreover, it should be noted that the device disclosed in the Wallace Canadian patent is not capable of being converted from automatic to manual operation. In other words, the device either operates automatically under the control of the motor, or it does not operate at all.

U.S. Pat. No. 2,545,865, also issued to Wallace, discloses a resectoscope which can be operated with one hand to both reciprocate the cutting element and control electrical energization of the cutting tip. This is representative of the prior art type of devices where reciprocation of the cutting tip only is carried out manually.

U.S. Pat. No. 3,149,633, issued to Zingale relates to a resectoscope wherein the tip is reciprocated by a pneumatic control system. In the Zingale device the cutting tip is not automatically reciprocated at a predetermined frequency. Instead, the exact position of the cutting tip is determined by the degree of depression of an actuating button 102. Thus, reciprocation of the cutting tip is achieved by sequentially depressing and releasing the button 102 to provide a manual mode of operation. Moreover, in the Zingale device the heating of the tip is not timed with the reciprocating motion. Rather, a separate foot control system is employed by the surgeon to manually energize the tip.

U.S. Pat. No. 4,196,734, issued to Harris, discloses a control system which can be used to apply either cutting or cauterizing current to a resectoscope. However, this patent is not in anyway concerned with a resectoscope adaptable for either manual or automatic operation, or a resectoscope wherein heating current is automatically timed with the reciprocating stroke of a cutting element to intermittently apply heat to the cutting tip during its cutting stroke.

U.S. Pat. No. 3,763,864, issued to Dremann, relates to an automatically powered, cold-punch resectoscope wherein the cutting tip is automatically reciprocated through the use of a hydraulic circuit. The Dremann device does not employ any heating means for energizing the cutting tip in view of the fact that the invention is directed to a cold-punch resectoscope. Moreover, there is no mechanism provided for converting the resectoscope from automatic to manual operation. In other words, like the Wallace device disclosed in earlier-referenced Canadian Pat. No. 452,125, the Dremann device either operates automatically under the control of the hydraulic circuit, or it does not operate at all.

OBJECTS OF THE INVENTION

It is an object of this invention to automate the cutting operation associated with intraurethral surgery on the prostate gland and/or bladder in a reliable and efficient manner.

It is a further object of this invention to provide a resectoscope which can either be operated manually by the surgeon or which can be operated automatically by a power source.

It is a further object of this invention to automatically control the heating of the cutting element of the resectoscope in a timed relationship to the cutting stroke thereof. It is a further object of this invention to provide for either manual or automatic operation of a resectoscope, depending upon the desires and needs of the surgeon.

It is a further object of this invention to provide for the simple and reliable control of the cutting and/or coagulating operations of a resectoscope.

SUMMARY OF THE INVENTION

The above and other objects of the invention are achieved by providing a resectoscope having a linearly movable cutting element mounted for reciprocating motion within an outer sheath adapted to be inserted into the urethra. A power source is provided for automatically reciprocating the cutting element when it is energized, and a control means, adapted to be actuated by the user, is provided for energizing the power source. In accordance with one aspect of this invention the power source for automatically reciprocating the cutting element also controls a timing means for intermittently completing an electrical circuit between a diathermy heating unit and the cutting element so that heat is applied to the cutting element during its cutting stroke. In accordance with another aspect of this invention the resectoscope either can be automatically operated or manually operated by appropriately setting a selector switch associated with the resectoscope.

Other objects and many of the attendant advantages of this invention will be readily appreciated as the same becomes better understood by reference to the following detailed description when considered in connection with the accompanying drawings.

BRIEF DESCRIPTION OF THE DRAWING

FIG. 1 is a longitudinal sectional view through a first embodiment of a resectoscope in accordance with this invention showing various details of construction;

FIG. 2 is an enlarged sectional view through the resectoscope taken along line 2—2 of FIG. 1;

FIG. 3 is a sectional view through the resectoscope taken along line 3—3 of FIG. 2;

FIG. 4 is an enlarged sectional view through the resectoscope taken along line 4—4 of FIG. 1;

FIG. 5 is an enlarged sectional view through the resectoscope taken along line 5—5 of FIG. 1;

FIG. 6 is an enlarged sectional view through the resectoscope taken along line 6—6 of FIG. 1;

FIG. 7 is an enlarged sectional view through the resectoscope taken along line 7—7 of FIG. 1;

FIG. 8 is an enlarged horizontal sectional view through the resectoscope taken along line 8—8 of FIG. 1;

FIG. 9 is an isometric view illustrating a portion of the system for manually reciprocating the cutter of the resectoscope illustrated in FIG. 1;

FIG. 12 is an enlarged side elevational view of the resectoscope from the side opposite that illustrated in FIG. 11;

FIG. 13 is a plan view of the resectoscope shown in FIGS. 11 and 12;

FIG. 14 is a sectional view taken along lines 14—14 of FIG. 12;

FIG. 15 is a sectional view taken along line 15—15 of FIG. 12;

FIG. 16 is an exploded isometric view of the selector switch illustrated in FIG. 15;

FIG. 19 is a sectional view taken along line 19—19 of FIG. 11;

FIG. 20 is a sectional view taken along line 20—20 of FIG. 11; and

DESCRIPTION OF THE PREFERRED EMBODIMENT

Figure 10:
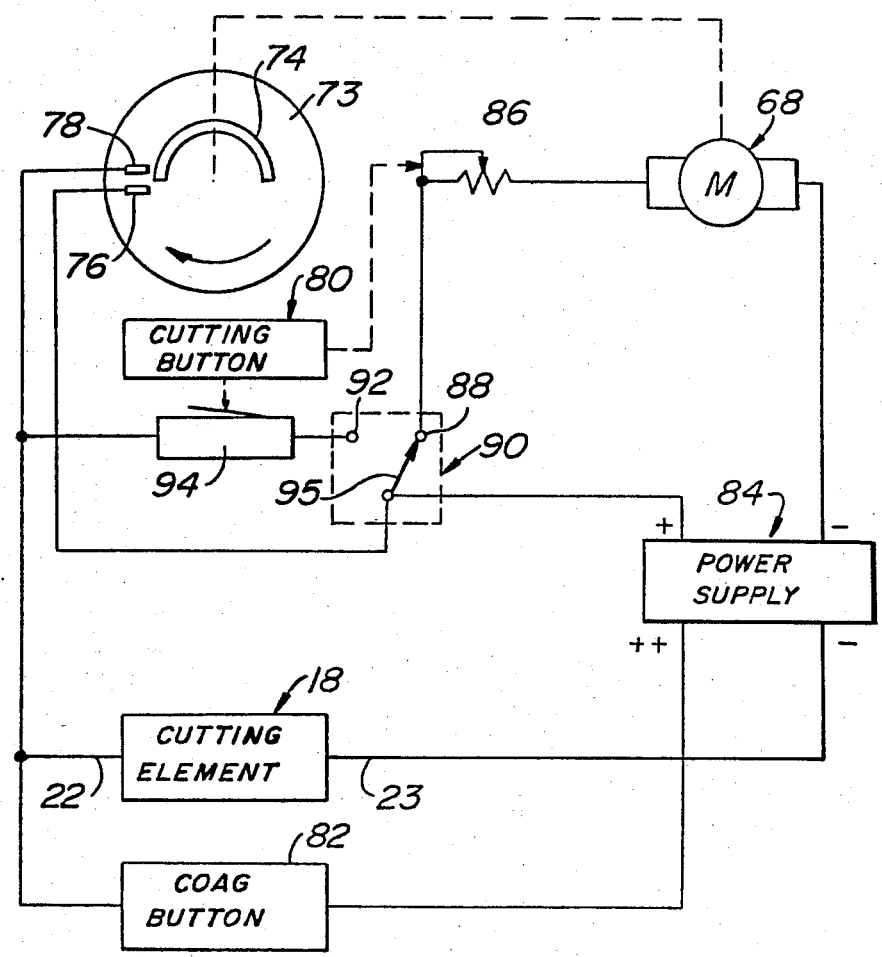
FIG. 10 is a schematic view of a representative circuit utilizable in accordance with the first embodiment of this invention.

Referring now in greater detail to the various figures of the drawings wherein like reference characters refer to like parts, a resectoscope embodying the present invention is generally shown at 10 in FIG. 1. The device 10 includes an outer sheath 12, preferably made of stainless steel, adapted to be inserted into the urethra for the purpose of performing either prostate or bladder surgery, as is well known in the art. Specifically, the outer sheath is inserted into the urethra to prevent it from collapsing, while the operative procedure is carried out utilizing working elements housed within said sheath.

Referring to FIGS. 1 and 8 a tubular working element 14 is located adjacent the downstream, or working end of the resectoscope, and is concentrically mounted within the outer sheath 12 thereof. Also housed within the interior of the sheath 12 and working element 14 is an elongate telescope 16. The telescope is of conventional construction includes a light source 15 and has an eye piece 17 for use in viewing the area of the prostate gland or bladder to be cut with the resectoscope.

Referring to FIGS. 1, 7 and 8 the resectoscope 10 includes an elongate cutting element 18. This element is of conventional construction and basically comprises a pair of spaced-apart, elongate, electrically insulated lead sections 22, 23 (FIG. 7), each formed of conductive wire having a diameter of approximately 0.5 mm, and an electrically heated tip 20 in the form of a semi-circular loop forming a bridge between the lead sections. The cutting element is designed to be reciprocated inwardly and outwardly of the sheath 12, with the cutting operation preferably performed on the inward stroke. Specifically, in a preferred manner of employing the resectoscope the cutting element 18 first is extended outwardly beyond the sheath 12 to position the tip 20 adjacent the area of tissue to be cut. Thereafter the tip 20 is heated while at the same time being retracted through a portion of tissue to be removed. If desired, the resectoscope actually can be rocked at the same time the cutting element is being retracted to thereby assist in cutting the tissue.

As is conventional, the resectoscope 10 of this invention also employs a continuous liquid irrigation system. Referring to FIG. 1, this system includes an inlet conduit 24 communicating with a source of sterile water or similar liquid (not shown) to provide the irrigating function. The conduit 24 is controlled by an inlet valve 26 to thereby regulate the amount of liquid directed into the downstream, or working end of the resectoscope. The incoming fluid flows in the direction indicated by the arrows 27 in a downstream direction through the interior of the working element 14. The liquid is forced to flow in this direction due to the arrangement of a bushing 28 sealing the rear, or upstream end of the working element. Referring to FIGS. 1 and 6, the bushing 28 includes openings for retaining the telescope 16 and the insulated leads 22 and 23 of the cutting element 18.

As the liquid flows out of the working element 14 it washes away blood and other debris that otherwise could obstruct the surgeon's line-of-sight through the telescope. The irrigating liquid then is removed from the surgery situs by flowing outwardly around the outer periphery of the sheath 12, and back into the chamber between the sheath 12 and working element 14 through a These passages 30 are exposed to a source of vacuum (not shown) through an outlet line 32 that is under the control of an outlet valve 34. By properly adjusting the inlet valve 26 and the outlet valve 34 the desired flow of irrigating liquid through the resectoscope can be provided.

In the preferred embodiment of this invention the downstream end of the stainless steel sheath 12 includes a heat resistant non-conductive tip 36 (e.g., fiberglass). This tip 36 prevents arcing between the heated tip 20 and the outer sheath 12, and also prevents the outer sheath from being excessively heated by said tip. Most preferably a plurality of return passages, only one being illustrated at 38 in FIG. 1, are provided in the heat resistant tip 36 to assist in removing the irrigating liquid from the bladder.

In accordance with the preferred embodiment of this invention, the device 20 includes means to effect the reciprocation and coordinated energization of the cutting tip either automatically or under manual control. The means for effecting such reciprocation and energization will now be considered. Thus, as can be seen best in FIGS. 1 and 5 the device 10 includes a stationary hand grip 40 secured about the sheath 12 and a movable handle 42. The movable handle includes spaced-apart legs 44, 45 through which a pivot pin 46 extends. This pivot pin also extends through opposed downwardly projecting lugs 47 of a substantially cylindrical clamp 48 that is frictionally secured about the outer periphery of the sheath 12. As can be seen best in FIG. 5 the spaced-apart legs 44, 45 of the handle also are rotatably secured by pins 50, 52 to a block 54 slidably mounted on the laterally spaced-apart insulated lead sections 22, 23 of the cutting element 18.

As can be seen best in FIGS. 1 and 9 the slidably mounted block 54 is mounted rearwardly of, but adjacent to a fixed block 56. This latter block is secured to the laterally spaced-apart insulated lead sections 22, 23 of the cutting element 18. The manner in which the movable block 54 cooperates with the fixed block 56 will be described in greater detail hereinafter.

A support 58 for the spaced-apart, insulated lead sections 22, 23 is fixed against movement to the outer periphery of the telescope 16, rearwardly of the slidably mounted block 54. The rear (free) ends of the leads extend through the support 58 and are joined to a connecting lug 60, the details of which are best illustrated in FIG. 4.

A tension spring is positioned about each of the laterally spaced-apart, insulated lead sections 22, 23 (only one spring being shown at 72 in FIG. 1), and these springs are biased between the fixed support 58 and the connecting lug 60. It also should be noted that the support 58 functions to limit movements of the handle 42 by being positioned to engage the movable block 54 attached to said handle.

Referring specifically to FIGS. 1, 2 and 4 a lever 62 is connected at one end to the lug 60, and at its opposite end to one end of a bell crank 64. The opposite end of the bell crank is fixed to rotate with a drive shaft 66 of a micromotor 68. The micromotor, which is the motive power source for the resectoscope, includes a connecting housing 70 provided with laterally extending flanges 71 directly bolted to the outer sheath 12.

Actuation of the motor 68 transmits the rotary motion of its drive shaft 66 into linear reciprocating motion of the cutting element 18 through the connection of the drive shaft to the cutting element by the bell crank 64, lever 62 and connecting lug 60. In the event that the motor is stopped with the cutting element 18 in its extended position, as shown in phantom in FIG. 1, the tension springs 72 automatically retract said element into the outer sheath of the resectoscope.

Referring specifically to FIGS. 2 and 3 a disk 73 is secured to the motor drive shaft 66 within the connecting housing 70 of the motor. As a result of this connection the disk 73 is adapted to rotate with the shaft 66, which, as explained above, controls the reciprocating motion of the cutting element 18. An arcuate electrical contact 74 is mounted in a fixed position adjacent said disk and bridges spaced-apart electrical contacts 76 and 78 to complete the circuit to the diathermy unit's power supply (not shown). This introduces high current into the cutting element 18, and in particular into the tip 20 thereof to thereby permit the cutting operation to be carried out.

The location of the contact 74 on the disk 73 is arranged to selectively bridge the contacts 76 and 78 for directing heating current into the tip 20 of the cutting element 18 when the cutting element is in its extended position, as indicated in phantom in FIG. 1. To that end, the circumferential, or arcuate dimension of the contact 74 is selected to maintain the heating current applied to the tip 20 as said tip is being retracted through its cutting stroke by the motor 68. In other words, both the position and circumferential length of the contact 74 are selected so that the heating cycle of the resectoscope 10 is timed to correspond with the cutting stroke of the cutting element Thus, the motor-driven contact 74 in conjunction with stationary contacts 76 and 78 constitute timing means for energizing the diathermy unit to heat the tip 20 of the cutting element 18 during the cutting stroke of said element.

The speed of rotation of the motor 68 is controllable. Thus, as can be seen in FIG. 1 the micromotor 68 includes a cutting speed control button 80 mounted on the movable handle 42. This button completes the motor energization circuit. Completion of this circuit causes the drive shaft 66 to rotate and thereby reciprocate the cutting element 18. At the same time the rotation of the drive shaft 66 completes the electrical circuit to the diathermy unit by engaging the arcuate contact 74 with the stationary contacts 76, 78 to thereby energize the cutting element.

The precise manner in which the circuitry is employed to control the reciprocation and energization of the cutting tip of the resectoscope 10 will be described in detail hereinafter in connection with FIG. 10. However, it should be noted that the speed control button 80 controls a potentiometer to increase the speed of reciprocation of the cutting element 18 as it is progressively depressed and to decrease the speed of reciprocation as it is progressively released. Thus, by the simple expedient of pressing the button 80 a desired amount the speed of reciprocation of the cutting element 18 can be precisely controlled. Moreover, the tip 20 of said cutting element automatically is heated during its cutting stroke by the timing circuit established by the motor-driven contact 74 and the stationary contacts 76 and 78.

As the cutting element 18 is being reciprocated automatically by the micromotor 68, the handle 42 is not reciprocated, but rather is maintained in the stationary position illustrated in FIG. 1. Reciprocating, or pivotal movement of the handle 42 about its pivot connection 46 is prevented by the securement of the handle to the slidably mounted block 54. This permits the lead sections 22, 23 to reciprocate within the block 54 without moving said block or handle 42 connected thereto. Therefore, during operation of the motor the handle will remain stationary and hence not interfere with the surgeon as a delicate cutting operation is being carried out.

In actual use the surgeon places his hand about the handle 42 and automatically controls the cutting cycle by merely depressing the button 80 the desired amount. Heating of the cutting element 18 occurs automatically on the retracting cutting stroke of the cutting element through the energizing of the diathermy unit by the earlier-described timing circuit.

Referring to FIG. 1 the fixed block 56 is secured to the laterally spaced-apart insulated leads 22 and 23 of the cutting element 18 in a position closely adjacent or confronting the slidably mounted block 54 when the handle 42 is fully extended and the cutting element 18 is fully retracted. Therefore, when the cutting element 18 is moved to an extended position with the tip 20 thereof outside the sheath 12 as shown in phantom in FIG. 1, the fixed block 56 is moved in a downstream direction to a position spaced from the block 54. When the cutting element is retracted, the fixed block 56 moves back to its position adjacent block 54. However, the block 56 will not move the block 54 and accordingly the handle 42 remains stationary.

A further unique feature of this invention resides in the ability to operate the resectoscope 10 either automatically or manually depending upon the desire of the surgeon. During the manual mode of operation the motor 68 is deenergized and the movable handle 42 is relied upon to reciprocate the cutting element 18 to provide the desired cutting action. To introduce heat energy to the tip 20 the cutting button 80 is depressed. This action closes a microswitch for completing a circuit through the diathermy unit. In the preferred operation of the resectoscope the button 80 is depressed manually to heat the tip 20 as said tip is being retracted from its extended position to thereby cut a desired piece of tissue.

Manual operation of the cutting element is accomplished by squeezing on the handle 42 to compress it toward the stationary hand grip 40. This causes the slidably mounted block 54 to press against and move the block 56 in a downstream direction. Since the block 56 is attached to the lead sections 22, 23 the cutting element 18 likewise will be forced outwardly beyond the heat resistant tip 36. Upon release of the hand grip the tension springs 72 retract the cutting element 18. This causes the block 56 to move against the slidably mounted block 54 and thereby force the handle 42 to move in a clockwise direction about its pivot pin 44 as viewed in FIG. 1. The degree of clockwise rotation of the handle 42 is limited by the location of the support 58 fixed to the telescope 16.

Referring specifically to FIG. 1 the handle 42 also includes an actuating button 82 to control the heating of the cutting element 18 when cauterization of a "bleeder" blood vessel is required. This button 82, referred to as a coagulation button, energizes the diathermy unit, when depressed, to introduce a cauterizing current through the cutting element 18 to cauterize the bleeder in a well known manner.

It should be noted that the coagulation, or cauterizing operation is intended to be carried out when the device 10 is in its manual mode of operation. In the automatic mode of operation the cutting element continuously is reciprocated, and therefore may not have the necessary residence time adjacent the bleeder to achieve effective cauterization. Thus, in order to provide the desired residence time for cauterization it is most desirable to carry out the cauterizing operation with the resectoscope 10 operated in its manual mode under the control of the surgeon.

Referring specifically to FIG. 10 representative circuitry utilizable with the invention will now be described, it being understood that various other circuits can be employed to accomplish the objectives of this invention.

In the circuit illustrated in FIG. 10 the micromotor 68 is serially connected to one pole of a power supply 84. That supply is a part of the diathermy unit. The other side of the motor is connected to one side of a potentiometer 86. The other side of the potentiometer is connected to its wiper arm and to a stationary contact 88 of a single pole double-throw selector switch 90. The contact 88 will be referred to hereinafter as the "automatic mode" contact. The selector switch also includes a second stationary contact 92. That contact will be referred to hereinafter as the "manual mode" contact of said switch. The stationary contact 92 is connected to one stationary contact of a microswitch 94. The movable contactor 95 of the single pole double-throw selector switch 90 is connected to the other pole of the power supply 86 and to a stationary contact 76 adjacent the arcuate contact 74 of the motor-driven disk 73. The other stationary contact of the microswitch 94 is connected to the stationary contact 78 and to one of the leads 22 of the cutting element. The other lead 23 of the cutting element is connected to the same pole of the power supply that is connected serially to the motor 68. The microswitch includes an actuating lever 96 which when depressed, causes the two stationary contacts of the microswitch to be in electrical contact with each other.

As is shown in FIG. 10 the microswitch 94 and the potentiometer 86 are both arranged to be operated by the depression of the cutting speed control button 80 on the handle 42 of the resectoscope. In the preferred arrangement both the microswitch and potentiometer are retained within a housing 96 mounted in the space between the laterally spaced-apart legs 44, 45 of the handle 42 (FIGS. 1 and 5).

When the selector switch is in the manual mode setting, i.e., contactor 95 is in contact with contact 92, and cutting button 80 is depressed the microswitch 94 is closed by the depression of its lever 96. Since the movable contactor 95 of the selector switch 90 engages contact 92, a circuit path as follows results: The positive side of the power supply 84 is connected through the movable contactor 95 and the stationary contact 92 to the microswitch 94. The microswitch is in its closed position due to the depression of the cutting button 80 and this connects the positive side of the power supply 86 to one side of the cutting element 18. The power supply 86 also is connected directly to the other side of the cutting element through its conductive lead 23. Accordingly, as long as that microswitch 94 is closed by the depression of the cutting button 80 with the selector switch 90 set in the manual mode power is supplied to the cutting element 18. It should be emphasized that in the manual mode of operation the motor 68 is out of the circuit and the button 80 functions only to energize the heating circuit to heat the cutting element 18.

It is understood that the surgeon using the resectoscope will depress the cutting button on the instroke of the cutting element 18, as is conventional. During the time that the cutting button 80 is maintained in a depressed condition the cutting tip 20 is energized to thereby effect the slicing of the prostate tissue.

In the automatic mode of operation the single pole double-throw selector switch 90 is moved to the automatic mode position with the movable contactor 95 thereof in contact with stationary contact 88. Although this single pole double-throw selector switch is not shown on the resectoscope, it is to be understood that it can be readily mounted thereon. Alternatively, it can be mounted as a floor switch and connected through a cable bundle 98 (FIG. 1) running to the resectoscope from the power supply 86.

As can be seen in FIG. 10 the coagulating button 82 is positioned within a circuit including the cutting element 18 and the power supply 84. When desired, the surgeon depresses the button 82 to provide a cauterizing current to the tip 20 of the cutting element 18.

Upon the movement of the selector switch to the automatic position the following circuit results: The positive side of the power supply (or the negative side if desired) is connected through the movable contactor 95 of the selector switch 90 and the stationary contact 88 to one side of the potentiometer 86. The other side of the potentiometer is connected to one side of the motor 68 and the other side of the motor is connected back to the power supply 86. Accordingly, the voltage is applied across the motor, with the magnitude of the voltage being established by the setting of the potentiometer 86, which in turn is controlled by the degree of depression of the button 80.

Depressing button 80 causes the motor 68 to commence rotating, thereby also rotating the disk 73 on the motor's output drive shaft 66. The rotary disk 73 includes the arcuate electrical contact 74 which is arranged to bridge stationary contacts 76 and 78 for approximately 180° of rotation of the motor, and when the cutting tip 20 is being reciprocated from its extended position to its retracted position. When the contacts 76 and 78 are bridged by arcuate contact 74 a circuit is completed from the power supply 84 to the cutting tip 20 to thereby heat the tip during the retracting stroke thereof. Specifically, the completed circuit is as follows: The positive side of the power supply 84 is connected to stationary contact 76, and the arcuate contact 74 of the rotary disk 73 bridges it and the stationary contact 78. Stationary contact 78 is connected to one side of the cutting element 18 through insulated lead section 22. The other side of the cutting tip is connected through its insulated lead section 23 to the other side of the power supply 84.

Under the automatic control of the micromotor 68 the speed of operation of the resectoscope can be varied within wide limits, i.e., from about 2 cuts per second to 1 cut about every 2 or 3 seconds. As explained earlier, the speed of operation is dictated by the degree of depression of button 80.

It is understood that power sources other than the illustrated micromotor 68 can be employed. For example, a motor can be located remote from the resectoscope, and can be provided with a suitable cable connection through a transmission to convert its mechanical driving motion into reciprocating motion of the cutting element 18. In fact, the resectoscope can be provided with a cable entrance port, and the motor for operating the cutting element could actually be located in a separate room, if desired.

It should be understood that the automatic operation of the motor could be effected by the use of a microprocessor and associated components which may conveniently be mounted in or on the handle or within the housing 96.

Referring now to FIGS. 11 through 21, the most preferred resectoscope in accordance with this invention is illustrated at 100. This resectoscope is a modified version of a conventional resectoscope manufactured by Storz in West Germany, and includes a manually actuatable operating handle 102 to which a selector switch 104 has been added for immobilizing the handle when the resectoscope is converted to automatic operation under the control of a power source 106. The power source is activated by simply depressing the hand actuatable button 107 of air switch 108, which button is secured to the handle 102.

Figure 11:
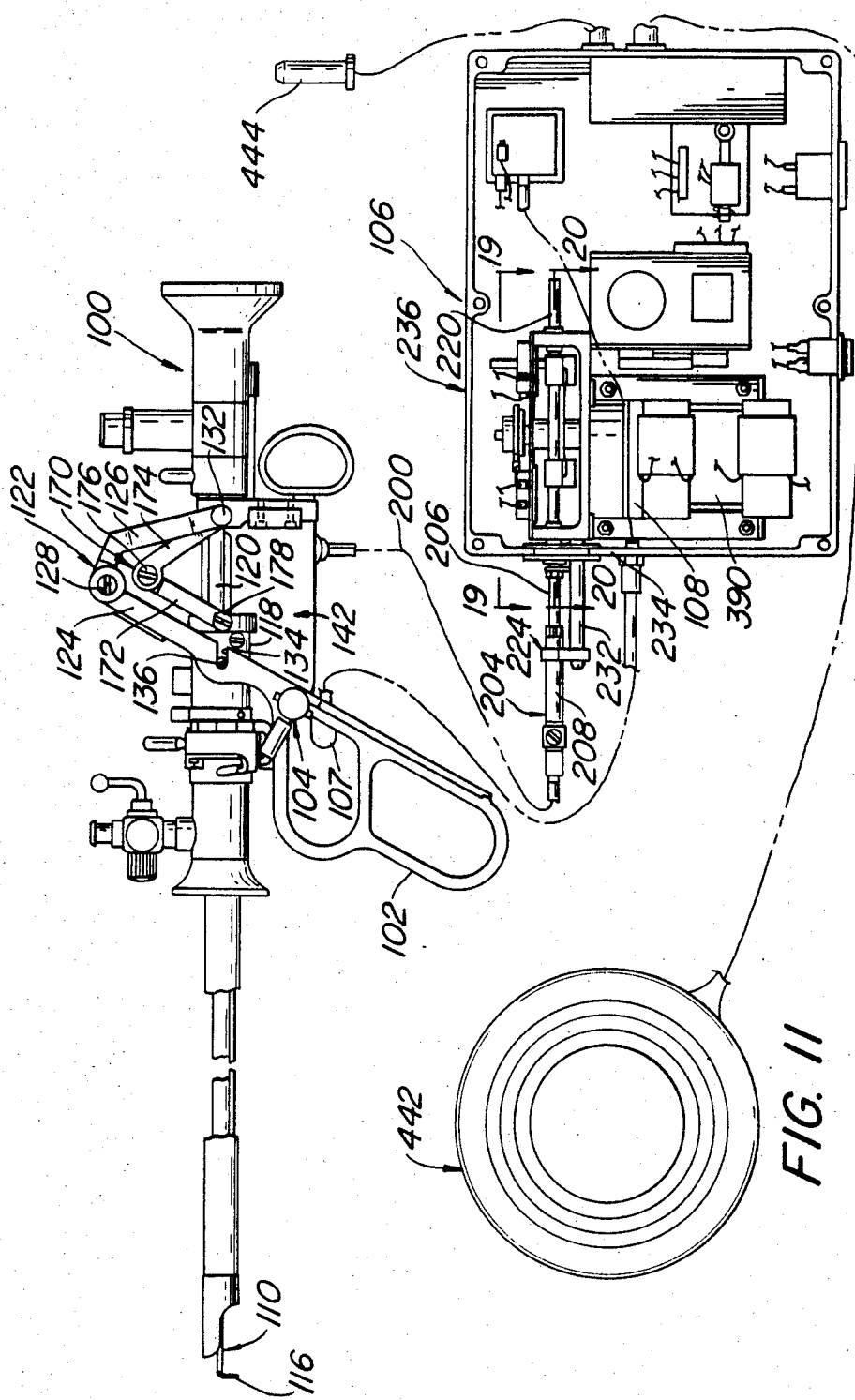
FIG. 11 illustrates the preferred construction of the resectoscope in accordance with this invention in side elevational view, and the power source for automatically operating the resectoscope on a reduced scale in plan view, with operating connections being shown in phantom lines.

Referring to FIGS. 11-13, the resectoscope 100 includes a conventional cutter 110 comprised of longitudinally extending conductive leads 112 and 114 provided with an interconnecting, U-shaped cutting tip 116. A cylindrical slide member 118 receives the rear ends of the conductive leads 112 and 114 in a conventional manner, and the slide member is mounted for reciprocating movement on a central rail 120 for the purpose of permitting the cutter 110 to be reciprocated to provide its intended cutting operation.

Still referring to FIGS. 11–13, a linkage system 122, which also is included in the conventional Storz resectoscope, includes a pair of links 124 and 126 pivotally connected to each other by a pivot member 128. As can be seen in FIG. 13, a coil spring 130 is mounted about the member 128 to normally bias the links 124 and 126 apart, to thereby normally maintain the cutter 110 in its outer position. The link 124 is screwed, or otherwise secured to the operating handle 102.

As can be seen best in FIGS. 11 and 13, the link 126 of the system 122 is provided with a fixed pivot connection 132 to the resectoscope. A generally U-shaped recess 134 is provided in the link 124, and this recess receives a pin 136 which is secured to the slide 118 and extends laterally therefrom.

Figure 17:
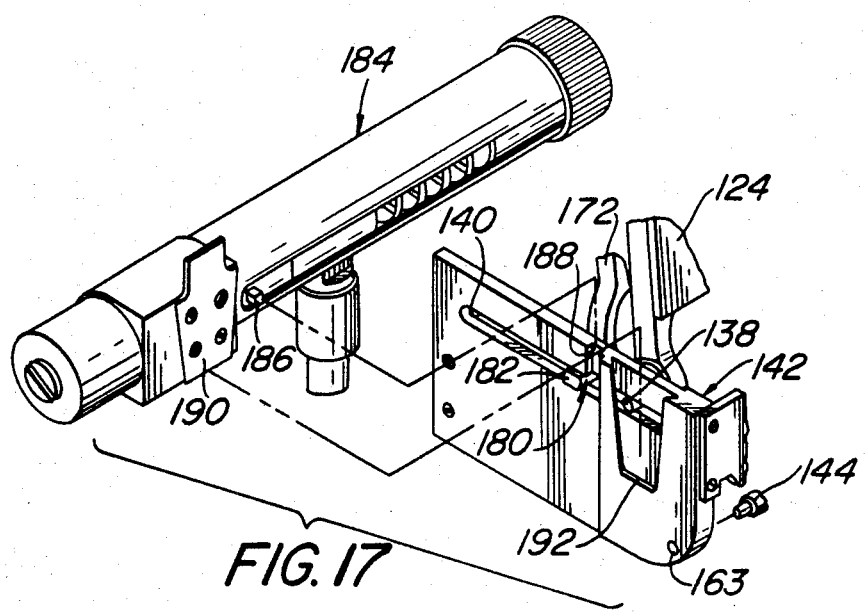
FIG. 17 is a fragmentary exploded isometric view illustrating the manner in which a single acting hydraulic cylinder cooperates with the resectoscope in accordance with this invention.

As can be seen best in FIGS. 17, a pin 138 is connected to the slide 118 and extends through an arm of link 124 in a location diametrically opposed to the pin 136. The pin 138 engages within an elongate guide slot 140 provided in a mounting plate 142. This mounting plate is employed to receive and retain a hydraulic cylinder employed in the automatic operation of the resectoscope, in a manner which will be described in detail later in this application. However, at this point it should be noted that the mounting plate assists in guiding the slide 118 as it is being moved linearly by the manual actuation of the handle 102 during convention manual operation of the resectoscope 100.

Referring to FIGS. 15 and 16, the details of the selector switch 104 are most clearly shown. This selector switch immobilizes the handle 102 so that it will not be movable during automatic operation of the resectoscope 100 under control of the power source 106. In this mode of operation the handle 102 is employed solely to hold or grip the resectoscope as the cutter 110 is being reciprocated automatically by operation of the power source 106.

The selector switch 104 includes a transversely extending locking pin 144 integrally formed with, or secured to a head 146. The head is provide with a laterally extending control handle 148 which is adapted to be manually grasped for controlling the movement of the locking pin between locking and unlocking positions of the switch. A ferrule 150 extends into a transverse opening 152 in the handle, and is welded to the link 124 which is connected to said handle. By virtue of the fact that the link 124 is connected to the handle, the ferrule 150 only is capable of moving with the handle. Stating this another way, by immobilizing the ferrule 150 so that it cannot be moved, the operating handle 102 also will be immobilized.

Still referring to FIGS. 15 and 16, the transversely extending locking pin 144 is both slideably and rotatably mounted within a central passage 154 extending through the ferrule 150. A movement-limiting lug 158 of the switch is firmly secured to the locking pin 144 with a screw 160, and this lug cooperates with the transversely spaced ferrule 150 to support a compression spring 162 therebetween. This compression spring normally biases the locking pin 144 into its locking position illustrated in FIG. 5 to immobilize the operating handle 102. Specifically, the end of the locking pin 144 opposite the head 146 is received within an opening 163 in the mounting plate 142 which, in turn, is fixed to the body of the resectoscope 100.

As can be seen best in FIG. 16, a pair of diametrically opposed pins 164 extend laterally from the outer body of the ferrule 150. These pins are adopted to engage within diametrically opposed recesses provided in the head 146 for the purpose of maintaining the selector switch either in a position for locking the operating handle 102 against movement, or for permitting the handle to be moved. Specifically, with diametrically opposed locking recesses 166 engaging the diametrically opposed pins 164, the compression spring 162 biases the locking pin 144 into engagement with the opening 163 in the mounting plate 142 to immobilize the handle.

To release the locking pin 144 from its engagement within the opening 163 in the mounting plate 142, and thereby permit the operating handle 102 to be manually actuated, the head 146 of the selector switch is rotated 90 degrees to bring diametrically opposed, shallower recesses 168 in the head 146 into engagement with the pins 164. In this latter position the locking pin 144 is biased out of engagement with the opening 163 in the mounting plate to permit the handle 102 to be manually moved.

It should be noted that a curved caming surface 169 partially defines each of the recesses 166 to provide for easy movement of the pins 164 out of engagement with the deeper recesses 166, and into locking engagement with the shallower recesses 168. In other words, the caming surface 169 makes it easy for a user to rotate the head 146 for permitting the locking pin 144 to be moved from its handle locking position to its handle unlocking position. The movement limiting lug 158 extends laterally from the locking pin 144 for engaging the inner surface 165 of the link 124 when the head 146 is rotated to a position at which the pins 164 are engaged within the shallow recesses 168.

Referring to FIGS. 11, 12 and 17, a unique feature of the resectoscope 100 resides in providing a second linkage system 170 which is employed for guiding the slide 118 during automatic operation of said resectoscope. Specifically the linkage system 170 includes a pair of links 172 and 174 pivotally connected to each other by a pivot member 176. A coil spring (not shown), identical to the coil spring 130, is disposed about the member 176 for the purpose of normally biasing the links 172 and 174 apart. In other words, the coil spring associated with the linkage system 170 operates in the same manner as the coil spring 130 associated with the linkage system 122. The fixed pivot connection 132 for the link 126 of the first linkage system also constitutes the fixed pivot connection for the link 174 of the second linkage system 170.

As can be seen best in FIG. 11, a screw 178 extends through the link 172 and is secured to the slide 118. This screw constitutes the pivot connection between the link 172 and said slide. As can be seen best in FIG. 17, a pin 180 is connected to the slide 118 and extends through the link 172 on the side of the slide opposed to the screw 178. This pin 180 includes a substantially flat head 182 which is mounted for sliding movement within the guide slot 140 of the mounting plate 142. The pin 180, unlike the pin 138, is an actuating pin that is adapted to be engaged for moving the linkage system 170, and the slide 118 secured thereto, when the operation of the resectoscope 100 is being controlled automatically by the power source 106. It should be noted that the automatic reciprocation of the slide 118 will, in turn, automatically reciprocate the cutter 110 secured thereto.

Referring specifically to FIGS. 13, 14 and 17, a single acting hydraulic cylinder 184 is employed for the purpose of reciprocating the cutter 110 under the control of the power source 106. This cylinder 184 includes an actuating pin 186 that is adapted to be slid through a vertical slot 188 in the mounting plate 142 into the guide slot 140, laterally adjacent the flat head 182. Thus, when the actuating pin 186 is moved through the operation of the hydraulic cylinder 184, it will actually move the link 172, the slide 118 attached thereto, and the cutter 110.

It should be noted that the actuating pin 186 is directed through the vertical slot 188 when the hydraulic cylinder 184 is attached to the resectoscope 110 through cooperating connectors 190 and 192, as is illustrated best in FIG. 17. Moreover, when the hydraulic cylinder 184 is operated to move the actuating pin 186, for the purpose of reciprocating the cutter 110, the hydraulic cylinder 184 cannot inadvertently separate from the mounting plate due to the fact that the actuating pin 186 will be out of alignment with the vertical slot 188. In other words, the actuating pin 186 will be trapped within the guide slot 140 to assist in positively retaining the hydraulic cylinder 184 on the mounting plate 142.

As can be seen best in FIG. 14, the actuating pin 186 forms an integral part of an internal housing 194 which is longitudinally movable outwardly relative to a fixed piston rod 196 by the introduction of hydraulic fluid within the interior of the housing 194 between end wall 198 and a sealed piston head 199. It should be noted that the sealed piston head is fixed the distal end of the piston rod 196.

As can be seen best in FIG. 12, a hydraulic line 200 directs hydraulic fluid into the interior of the housing 194 for moving the housing outwardly relative to the piston rod 196 against the compressive force of a compression spring 202. This outward movement of the internal housing will move the actuating pin 186 against the flat head 182 of the pin 180 to thereby move the lever 172 inwardly toward lever 174 to retract the cutter 110.

Figure 18:
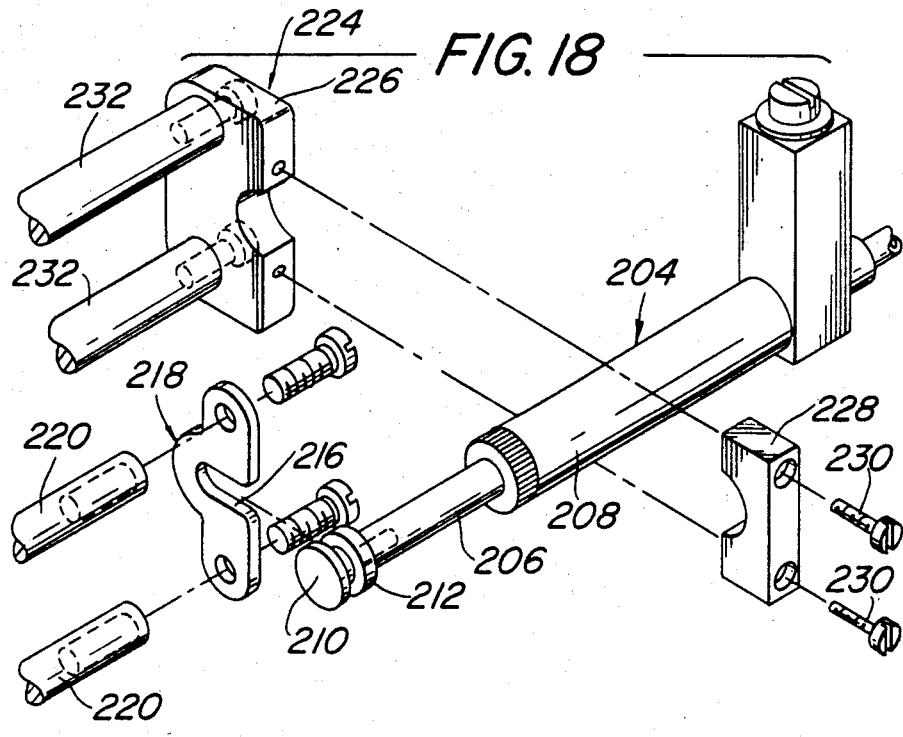
FIG. 18 is a fragmentary exploded isometric view illustrating the arrangement for connecting the power source to a hydraulic cylinder for automatically controlling the operation of the resectoscope.

As can be seen best in FIGS. 11 and 18, a second hydraulic cylinder 204 is employed for the purpose of forcing hydraulic fluid into the internal housing 194 of the cylinder 184 through the line 200. The cylinder 204 includes a piston rod 206 extending into an outer housing 208. The piston rod 206 is positively driven through the operation of the power source 106 by an interconnection which is most specifically shown in FIG. 18.

Referring to FIG. 18 the piston rod 206 includes an enlarged head 210 and an axially spaced, enlarged flange 212 defining an annular groove therebetween. This groove is received within a U-shaped slot 216 of a clevis 218. The clevis is secured to reciprocable rods 220 by screws 222, and reciprocation of the rods 220 is controlled by the operation of the power source 106 in a manner to be described in detail hereinafter. Thus, reciprocation of the rods 220 will positively move the piston rod 206 into and out of the housing 208.

Movement of the piston rod 206 into the housing 208 forces hydraulic fluid through the line 200 and into the single acting hydraulic cylinder 184 for the purpose of retracting the cutter 110. Movement of the piston rod 206 out of the housing 208 permits the compression spring 202 within the hydraulic cylinder 184 to force the internal housing 194 thereof inwardly toward the fixed piston rod 196 to force hydraulic fluid out of the housing 194, through the line 200 and into the housing 208 of the hydraulic cylinder 204. This inward movement of the internal housing 194 permits the coil spring connecting the links 172 and 174 to move said links apart, and thereby extend the cutter 110.

As can be seen best in FIGS. 11 and 18, the mounting of the hydraulic cylinder 204 is completed by a clamp 224 including opposed clamping plates 226 and 228 which are adapted to be secured about the body of the housing 208 with interconnecting screws 230. A pair of support rods 232 are secured to one of the clamping plates 220, and these rods are bolted to an end wall 234 of a housing 236 for the power supply 106.

Having described the overall arrangement of elements in the resectoscope 100, the circuit arrangement for controlling the automatic operation of said resectoscope will now be described with reference to FIGS. 11 and 19-21.

Figure 21:
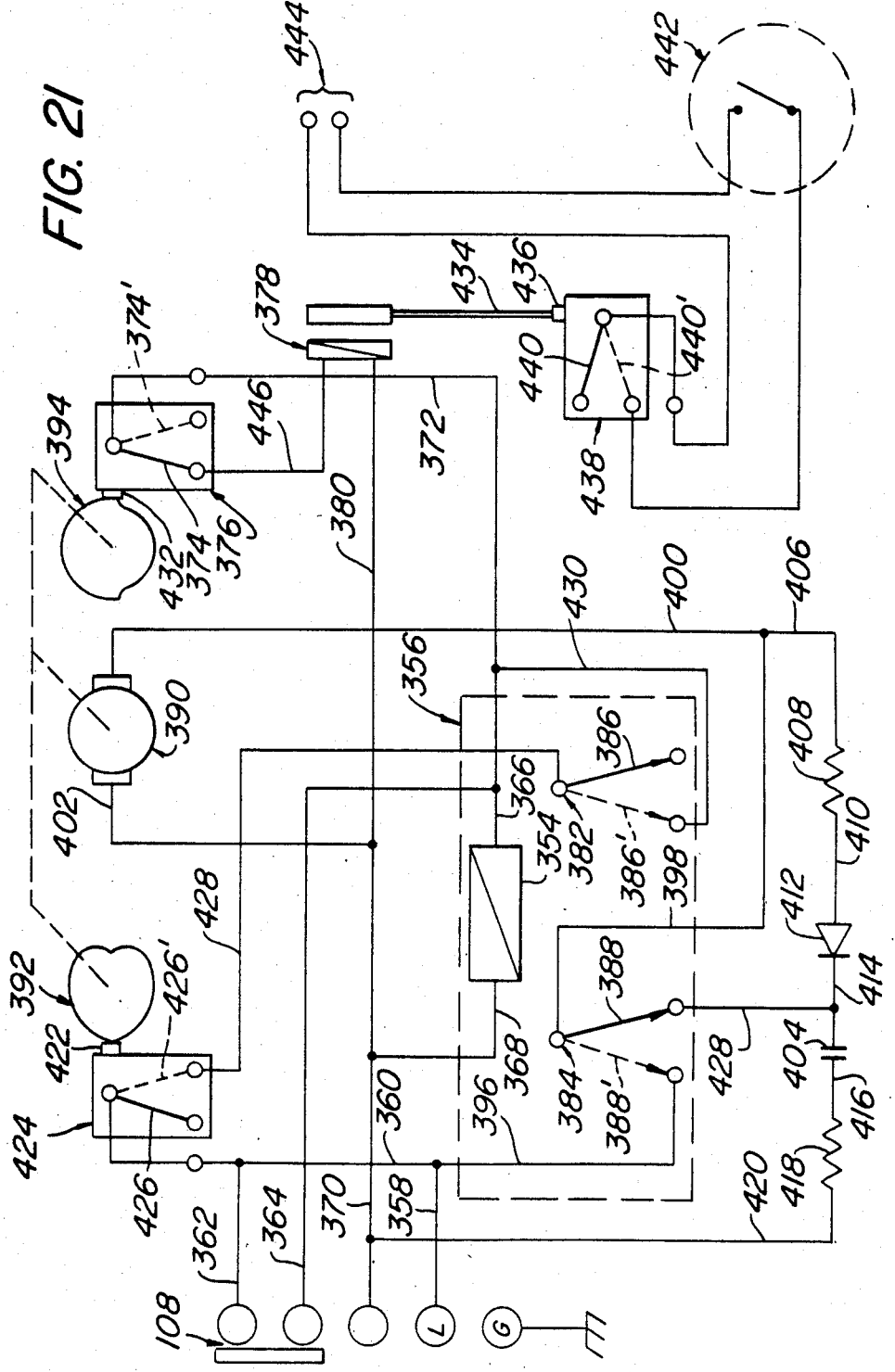
FIG. 21 is a schematic diagram of the circuit arrangement employed for controlling the operation of the resectoscope.

Referring specifically to FIGS. 11 and 21, the automatic operation of the resectoscope 100 is commenced by pressing button 107 on handle 102 to close the air switch 108. This completes a circuit from the line voltage, L, to the relay coil 354 of relay 356. Specifically the circuit is completed through conductor lines 358, 360, 362, 364, 366, 368 and return line 370. Thus, as long as the button 107 is depressed to close switch 108 the relay 356 will remain energized. It should be noted that closing the switch 108 also establishes a current flow path through conductive line 372 and the movable contact 374 of microswitch 376. In addition, a current flow path is established to solenoid 378 through conductive line 380. It should further be noted that the circuit through the solenoid 378 is not completed until such time as the movable contact 374 of the microswitch 376 moves to the dotted line position indicated at 374'.

Energizing the relay coil 354 automatically actuates relay switches 382 and 384 to cause their movable contacts 386 and 388, respectively, to move from the positions represented in solid lines to the dotted line positions indicated at 386' and 388' respectively.

Movement of contact 388 to the position indicated at 388' completes the circuit to the drive motor 390. The motor 390 drives cams 392 and 394, through a conventional gearbox, at a speed of approximately 100 cycles per minute. The motor circuit is completed through conductive lines 358, 396, 398 (with the movable contact 388 in position indicated at 388'), 400, 402 and 370.

Therefore, as long as switch 108 is closed the relay coil 354 will remain energized, and the motor 390 will continuously operate to continuously rotate the cams 392 and 394.

With the movable contact 388 of the microswitch 384 in the position indicated at 388', a circuit also is completed to charge capacitor 404. The charged capacitor is utilized to stop the motor 390 quickly, in a manner which will be explained hereinafter.

The circuit for charging the capacitor is completed through conductor lines 358, 396, 398, 406, resistor 408, conductive line 410, diode 412, conductive line 414, conductive line 416, resistor 418, conductive line 420 and return conductive line 370. Note that the circuit to the capacitor 404, for purposes of charging it, does not include the motor 390 in it. However, as will be explained later, the capacitor will be connected across the motor 390 when it is desired to stop the motor.

Movement of the movable contact 386 of the relay switch 382 to the position indicated at 386' locks the relay 356 in the energized state when the cam 392 causes operating lever 422 of microswitch 424 to be released, thereby positioning the movable contact 426 of said microswitch in the position 426' shown in dotted line representation in FIG. 21. When the movable contact 426 is in this dotted line position, the relay 356 will remain energized to thereby maintain the energizing voltage across the motor 390 for the purpose of driving cams 392 and 394, even with the switch 108 opened. When the cam 392 is rotated to a position wherein the lever 422 of the microswitch 424 is depressed as is shown in FIG. 21, to thereby move the movable contact 426 to the solid line position indicated at 426', the voltage to the relay coil 354 will be interrupted, allowing the relay 356 to drop out of the circuit and cause the movable contacts 386 and 388 of the relay switches 382 and 384, respectively, to move into the sold line positions indicated in FIG. 21. Of course this only occurs when the switch 108 is opened. If the switch 108 is maintained in a closed condition, then the relay 356 will be continuously energized, and the motor 390 will be continuously driven.

Referring to FIG. 21 when the cam 392 is moved to release the lever 422 of the microswitch 424, the circuit to relay coil 354 is maintained through line 360, microswitch 424, line 428, relay switch 382, line 430, line 366, line 368 and return line 370. When the cam 392 actuates the operating lever 422 of the microswitch 424 to close it, the movable contact 426 will move into the solid line position indicated at 426' to break the relay circuit established through the microswitch. Accordingly, if the switch 108 likewise is opened, there will be no current applied to the relay coil 354, thereby resulting in the relay dropping out of the circuit.

When the relay 356 is not in the circuit, the movable contacts of the relay switches 382 and 384 will move into the solid line positions indicated at 386, 388, respectively, in FIG. 21. With the contact 388 in the solid line position indicated in FIG. 21, the capacitor 404 is placed in the circuit of motor 390. This capacitor preferably is charged up to a value approaching the full rectified AC voltage. Therefore, by placing this capacitance in the motor circuit, the motor will be stopped quickly, thereby preventing any overrun which could create undesired reciprocation of the cutter 110 of the resectoscope.

The capacitor 404 is placed in the motor circuit through conductive line 428, relay switch 384, conductive line 398, conductive line 400, conductive line 402 and return conductive line 370.

Referring specifically to FIGS. 11, 19 and 21, the cam 394 controls the operation of microswitch 376 for the purpose of automatically controlling the heating cycle of the resectoscope in timed sequence with the cutting stroke of the cutter 110. In particular, when the cam 394 engages operating lever 432 of microswitch 376, as is shown in FIGS. 19 and 21, it will cause the movable contact 374 thereof to be positioned in the solid line position indicated at 374. This completes a circuit through the solenoid 378 which, in turn, actuates a push rod 434 connected to an operating lever 436 of a microswitch 438. The microswitch 438 includes a movable contact 440 which is moved into the dotted line position indicated at 440' at FIG. 21 when the operating lever 436 is depressed by the push rod 434.

Referring to FIGS. 11 and 21, the system further includes a foot switch 442 connected in series with a diathermy unit (not shown) which is connected to outlet plug 444. In order to complete the circuit to the diathermy unit the foot switch 442 needs to be closed by depressing it, and the solenoid 378 energized to move contact 440 of the microswitch 438 into the dotted line position indicated at 440'. With the foot switch 442 closed, the energizing of the diathermy unit to heat the cutter 110 of the resectoscope is under the control of the cam 394 and microswitch 376. Rotation of the cam 394 under control of the motor 390 intermittently completes the circuit through the diathermy unit for approximately one-half of the reciprocating cycle of the cutter 110. In particular, the cam 394 is designed so that the cutter is heated during the retracting portion of its stroke when it is providing a cutting operation.

Referring to FIG. 21, when the operating air switch 108 of the resectoscope is closed, the circuit to the solenoid 378 is completed through conductive lines 358, 360, 362, 364, 372, microswitch 376, conductive line 446 and return lines 380 and 370. Thus, it is only when the movable contact of microswitch 376 is in the solid line position indicated at 374 that the circuit to the solenoid is completed, and the movable contact only is in this position during the portion of the operating cycle of the resectoscope when the cam 394 depresses the operating lever 432 of the microswitch 376. Since the cam 394 is designed to depress the lever during only one half of each operating cycle of the cutter 110, this automatically controls the operation of the diathermy unit to heat the cutter during this same period of time.

It should be noted that the circuit through the solenoid 378 also is complete when cam 392 releases the operating lever 422 of the microswitch 424 to cause the movable contact to move into the dotted line position indicated at 426', due to the fact that the movable contact of the relay 382 is in the dotted line position indicated at 386'. Specifically, when the cam 392 releases the operating lever 422 of the microswitch 424, and air switch 108 is opened, the circuit through the solenoid 378 will be established through conductive lines 358, 360, microswitch 424, conductive line 428, relay switch 382, conductive line 430, conductive line 372, microswitch 376, conductive line 446 and return lines 380 and 370. Of course, when the cam 392 moves to a position for depressing the operating lever 422 of the microswitch 424, which is its normal at-rest position, and thereby positions the contact 426 in the solid line position 426, the circuit through the solenoid 378 will be opened, assuming that the air switch 108 is opened.

Referring specifically to FIGS. 11 and 18–20, the cam 392 is mounted on the driven shaft of the motor 390 and is positioned between cooperating abutments 454 and 456 that are attached to the reciprocating rods 220 secured to the clevis 218. As explained earlier, the clevis 218 is secured to the piston rod 206 to move it into and out of the housing 208 of the hydraulic cylinder 204. Movement of the piston rod 206 into the housing 208 forces hydraulic fluid through line 200 to cause the hydraulic cylinder 184 attached to the resectoscope to retract the cutter 110. Movement of the piston rod 206 out of the housing 208 permits the compression spring 202 of the cylinder 184 to function to extend the cutter 110.

Referring to FIGS. 19, 20 and 21, abutment 454 includes a switch operating projection 458 which depresses the operating lever 422 of the microswitch 424 to position the movable contact thereof into the solid line position indicated at 426 in FIG. 21. This occurs at the end of the retracting stroke of the rods 220, which moves the piston rod 206 outwardly from its cooperating housing 208. It should be noted that as the rods 220 are being retracted the compression spring 202 of the hydraulic cylinder 184 connected to the resectoscope (FIG. 3) functions to extend the cutter 110. It is at the end of this retracting stroke of the rods 220, which corresponds to the extension stroke of the cutter 110, that the microswitch 424 is operated to disengage the relay 356 and stop the drive motor 390, assuming of course that the air switch 108 is opened. If the switch 108 is closed by the surgeon, then the depression of the lever 422 of the microswitch 424 will not have any effect on the operation of the system. In other words the cutter 110 will be continuously reciprocated.

It should be noted that when the air switch 108 is opened, the cam 394 automatically is positioned to depress the operating lever 432 of the microswitch 376 through the operation of relay 356. This positions the movable contact 374 in the solid line position indicated in FIG. 21 to complete the circuit through the solenoid 378. Actuation of the solenoid 378 positions the movable contact 440 in the dotted line position indicated at 440' in FIG. 21 to permit the circuit through the diathermy unit to be completed by merely depressing the foot switch 442. This is precisely the manner in which the heating of the cutter 110 is carried out during manual operation of the resectoscope. In other words, during manual operation of the resectoscope the surgeon depresses the foot switch 442 to close the heating circuit to the diathermy unit as he or she retracts the cutter 110 to remove undesired tissue, or when the cutter is maintained in an extended position to perform a cauterizing operation.

Without further elaboration the foregoing will so fully illustrate my invention that others may, by applying current or future knowledge, adopt the same for use under various conditions of service.

I claim:

1. A resectoscope having means to view the operative field during the operation of said resectoscope, said resectoscope corprising a linearly movable cutter mounted for reciprocation within an outer sheath, characterized by a power source for automatically reciprocating the cutter when said source is energized to move said cutter through a pair of strokes, one stroke extending said cutter from said sheath and the other stroke retracting said cutter to said sheath, with only one of said strokes serving as a cutting stroke, control means actuatable by a user for energizing the power source, manually operable, hand actuatable lever means interconnected with the cutter and arranged to be moved by the user for effecting manual reciprocation of the cutter through at least one of said pair of strokes under control of the lever means independently of the operation of the power source, said hand actuatable lever means being decoupled from said power source so that said means is not moved during automatic reciprocation of said cutter.

2. The resectoscope of claim 1 characterized by selector switch means for immobilizing the lever means during automatic operation of the resectoscope under control of the power source.

3. The resectoscope of claim 2 characterized by a switch means for manually energizing a heating means when the selector switch means is set for the manual mode.

4. A resectoscope having means to view the operative field during operation of said resectoscope, said resectoscope comprising an outer sheath and a linearly movable cutter mounted for reciprocation with respect to said outer sheath, characterized by a power source coupled to said cutter for automatically reciprocating the cutter when said source is energized to move said cutter in a first direction to an extended position and in a second and opposite direction to a retracted position, with the movement in one of said two directions defining a cutting stroke, control means actuatable by a user for energizing the power source, heating means for transmitting electrical heating current to said cutter, automatic timing means coordinated with said cutting means for intermittently energizing the heating means so that the cutter is energized only during the cutting stroke thereof and manually actuatable means for manually reciprocating said cutter, said manually actuatable means being decoupled from said power source so that said manually actuatable means is not moved during automatic reciprocation of said cutter.

5. The resectoscope of claim 1 characterized in that the power source for automatically reciprocating the cutter also controls the timing means.

6. The resectoscope of claim 1 characterized by relay means actuated by the control means for assuring that the cutter reciprocates through at least one complete cycle upon actuation of the control means.

7. The resectoscope of claim 1 characterized in that said control means includes an actuating member on said resectoscope.

8. The resectoscope of claim 1 characterized by the inclusion of switch means for energizing the heating means independently of the timing means to thereby permit heating of the cutter while said cutter is maintained in a desired position for cauterization of body tissue.

9. The resectoscope of claim 1 characterized by a hand actuatable lever means interconnected with the cutter and adapted to be manually actuated by the user to reciprocate the cutter independently of the operation of the power source.

10. The resectoscope of claim 9 characterized by switch means for immobilizing the lever means during automatic operation of the resectoscope under control of the power source.

11. The resectoscope of claim 1 characterized in that the power source includes a first cam that is driven for controlling the operation of a fluid cylinder which, in turn, controls reciprocating movement of the cutter.

12. The resectoscope of claim 11 characterized in that the timing means includes a second cam driven with said first cam for intermittently actuating a switch for completing a circuit to energize the heating means.

13. The resectoscope of claim 1 characterized in that the timing means is automatically responsive to the speed of reciprocation of the cutter for permitting the speed of reciprocation of said cutter to be varied while still energizing the heating means during said cutting stroke.

14. The resectoscope of claim 13 characterized by variable speed control means controlling the speed of reciprocation of said cutter and the timing means responsive to said speed of reciprocation, and coagulating switch means indepedent of the variable speed control means for energizing the heating means independently of the timing means to permit heating of the cutter while the cutter is maintained in a desired position for cauterization of body tissue.

15. The resectoscope of claim 14 characterized by a handle manually engageable by a user of the resectoscope, an actuating member of said variable speed control means and an actuating member of said coagulation switch means being disposed on said handle.

16. The resectoscope of claim 13 characterized by variable speed control means for varying the speed of reciprocation of said cutter.

17. The resectoscope of claim 16 characterized by the inclusion of a handle adapted to be gripped by a user, said variable speed control means including an actuating member on said handle.

* * * * *